(12) United States Patent
Schoellhorn

(10) Patent No.: US 7,575,546 B2
(45) Date of Patent: Aug. 18, 2009

(54) HEART HOLDER

(75) Inventor: Joachim Schoellhorn, Freiburg (DE)

(73) Assignee: Karl Storz GmbH & Co. KG (DE)

( * ) Notice: Subject to any disclaimer, the term of this patent is extended or adjusted under 35 U.S.C. 154(b) by 758 days.

(21) Appl. No.: 10/914,668

(22) Filed: Aug. 9, 2004

(65) Prior Publication Data
US 2005/0038324 A1    Feb. 17, 2005

Related U.S. Application Data

(63) Continuation of application No. PCT/EP03/01206, filed on Feb. 7, 2003.

(30) Foreign Application Priority Data

Feb. 8, 2002   (EP) .................................. 02002860

(51) Int. Cl.
*A61B 1/32* (2006.01)
(52) U.S. Cl. ...................................................... 600/37
(58) Field of Classification Search ............ 600/37, 600/201, 204, 206, 210, 211, 214, 229, 235; 128/897, 898
See application file for complete search history.

(56) References Cited

U.S. PATENT DOCUMENTS

| | | | | |
|---|---|---|---|---|
| 4,048,987 A | * | 9/1977 | Hurson | 600/206 |
| 5,080,088 A | * | 1/1992 | LeVahn | 600/206 |
| 5,381,788 A | * | 1/1995 | Matula et al. | 600/214 |
| 5,722,935 A | | 3/1998 | Christian | 600/214 |
| 5,894,843 A | * | 4/1999 | Benetti et al. | 128/898 |
| 5,947,896 A | * | 9/1999 | Sherts et al. | 600/229 |
| 6,019,722 A | * | 2/2000 | Spence et al. | 600/210 |
| 6,102,854 A | | 8/2000 | Cartier et al. | 600/228 |
| 6,146,401 A | | 11/2000 | Yoon et al. | 606/192 |
| 6,506,149 B2 | * | 1/2003 | Peng et al. | 600/37 |

FOREIGN PATENT DOCUMENTS

WO   WO 98/49947   11/1998

* cited by examiner

*Primary Examiner*—Samuel G Gilbert
(74) *Attorney, Agent, or Firm*—St. Onge Steward Johnston & Reens LLC

(57) ABSTRACT

A functional element to be mounted on a retractor for performing cardiothoracic surgery has a securing device for mounting it releasably on the retractor. A device for holding up a beating heart lifted from an operating site has several spreadable strip-shaped holding fingers. It is proposed that three or four strip-shaped holding fingers are present which are designed to be bendable so that they can be shaped to form a holding basket adapted to the particular heart which is to be held.

8 Claims, 5 Drawing Sheets

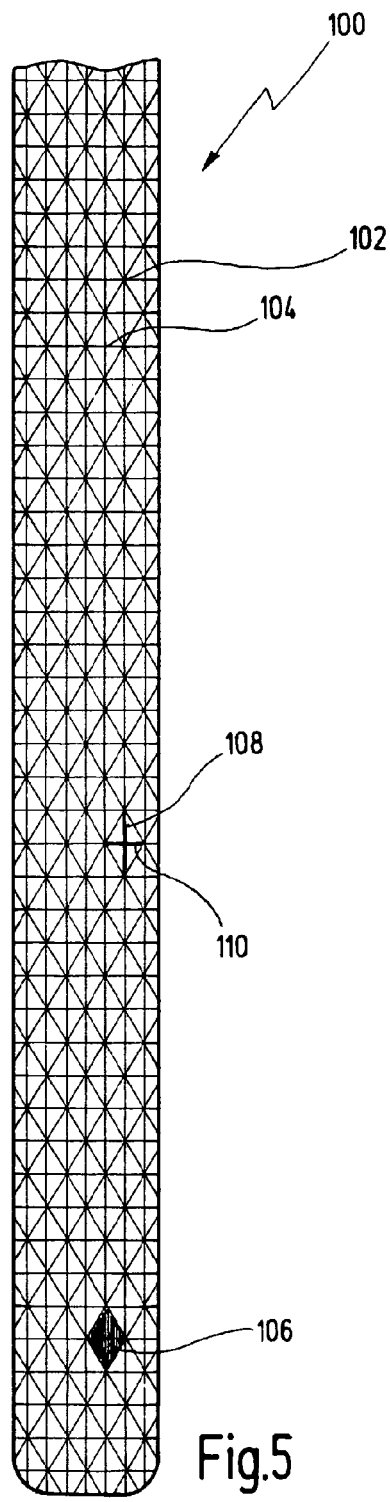
Fig.5
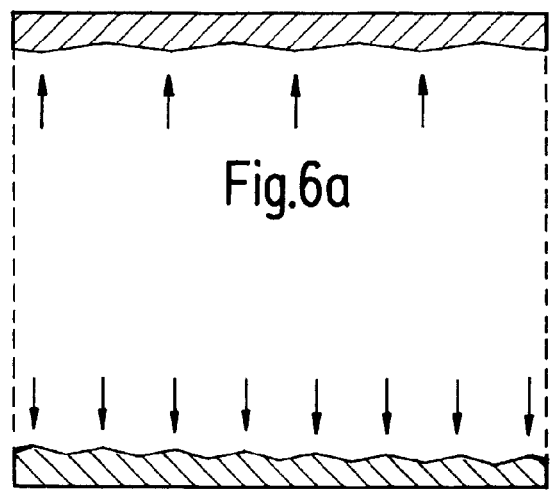
Fig.6a
Fig.6b

HEART HOLDER

CROSSREFERENCE OF PENDING APPLICATION

This application is a continuation of pending international application PCT/EP03/01206 filed on Feb. 7, 2003 which designates US and which claims priority of European patent application No. 02 002 860.1 filed on Feb. 8, 2002.

BACKGROUND OF THE INVENTION

The present invention relates to a functional element to be mounted on a retractor for performing cardiothoracic surgery, with a securing device for mounting it releasably on the retractor, and with a device which is used for holding up a beating heart lifted from an operating site and has several spreadable strip-shaped holding fingers.

A functional element of this kind is known from U.S. Pat. No. 6,019,722.

A retractor has a toothed rail, from which a first holding rail is angled off, and a second holding rail which can be driven along the toothed rail via a drive mechanism and which extends parallel to the first holding rail and can be moved toward and away from the latter.

Various functional elements can be mounted releasably on the holding rails.

Retractors of this kind are used, for example, as rib retractors in operations performed on an open and beating heart. The specialist terms thoracic retractor and sternal retractor have also become established for these. When using a sternal retractor, the sternum is divided along its length, and hook-shaped functional elements both on the fixed holding rail and on the movable holding rail are introduced into the surgical opening. By actuating the drive mechanism, the movable and the fixed holding rails are moved away from one another and, in the process, the thoracic cage is spread and an access opening is created through which the operating surgeon can perform surgical procedures in particular on the beating heart.

Further functional elements can be mounted releasably on the holding rails in order to assist the operating surgeon during the operation.

An example of these further functional elements is a Leyla retractor, which is used as an auxiliary instrument for suturing blood vessels. Other functional elements are MIDCAB (minimal invasive direct coronary artery bypass) retractors or IMA retractors for access to the internal thoracic artery, which are used to lift that half of the thorax in which the heart is located in relation to the other half of the thorax, so as obtain further improved access to the heart.

A device which is used for holding up a beating heart lifted from an operating site and which has several spreadable strip-shaped holding fingers is known from U.S. Pat. No. 6,019,722. With this device, a beating heart can be lifted out from the opened thoracic space via its apex and can be held in this position, by which means it is possible to access the posterior wall of the heart in order to operate there. Since the heart is still beating, the problem which arises is that of holding a pulsating organ in a lifted position for the duration of an operation.

The holding device in U.S. Pat. No. 6,019,722 has two types of holding elements. A first type, referred to in said document as a rigid cross support, is made of a rigid non-bendable material. In a first embodiment, this first type is designed as a kind of cup in which the apex of the heart can be placed. The main weight of the heart is carried by the cup. In addition, the heart is sucked into the cup by means of a vacuum. In a further embodiment, this first type consists of two spreadable strip-shaped stiff holding fingers which are applied in the area of the apex of the heart and extend approximately about the circumference of the apex. The apex of the heart is clamped between the stiff holding fingers, and here too suction openings are provided for suctioning the heart.

Moreover, a second type of holding element must be provided, namely respectively at least four further elastically rod-shaped elements extending substantially in the longitudinal direction of the heart. These four holding elements of the second type are bendable and, at their outer ends, they each have a suction cup. By applying a vacuum, and by virtue of their pliability, these four holding elements of the second type can follow the pulsating contraction movements of the beating heart. They are thus able to move substantially in radial directions, viewed in relation to the longitudinal axis of the heart, and for this purpose are movable. In said document, this second type is referred to as a fine support means. In the embodiment with the spreadable strip-shaped holding fingers, there are therefore six holding elements in total, two of the first type and four of the second type, which ensure that the beating heart is held up. The basic principle of this heart holder is to support the main weight of the heart in the area of its apex via the rigid cross support (gross weight support means) and additionally to immobilize it by vacuum. The elastic fine support means are used for lateral support and follow the contraction movements of the heart.

Because so many holding elements, namely six, are present, it is necessary to have a large number of bearing points and holding points on the outer surface of the heart, but this necessarily restricts or obstructs the access to the heart. The purpose of lifting the heart is after all to gain access the outside of the beating heart, in particular to the posterior wall of the heart, and perform surgery there. The cage consisting of a total of six holding fingers considerably impedes this access, however.

Moreover, the construction is extremely complex and necessitates production and handling of two completely different types of holding elements.

It is therefore an object of the present invention to make available a functional element of this type which is of much simpler design, is easier to handle and causes less obstruction of the held heart, but which still guarantees that the heart is held up securely.

SUMMARY OF THE INVENTION

According to the invention, the object is achieved by the fact that merely three or four strip-shaped holding fingers are present which are designed to be bendable so that they can be shaped to form a holding basket adapted to the particular heart which is to be held.

It has been found that it is possible to securely hold a beating heart with a single type of holding element, specifically if this is done with three spreadable strip-shaped holding fingers made of a material which is bendable so that each strip can be adapted to the particular heart which is to be held.

By this means, these three strips can be shaped in situ to form a holding basket in which the beating heart can be received and can be held securely. The spreadability, which is known per se, means that the three strips can be opened out in a fan shape and placed against the heart in such a way that the latter does not slip out laterally between the holding fingers. Because they are bendable, the strips can be adapted to the particular anatomy of the heart to be lifted or to the heart apex.

Particularly in heart patients on whom such operations are performed, the heart exhibits pathological changes in form, so that, by virtue of their bendable nature, the strips can be adapted to the individual circumstances of the heart shape. In this way, an individual holding basket can be formed which securely holds up the lifted heart and still permits the pulsating movements of the heart inside the formed holding basket. A basket made up of only three fingers leaves three self-contained unobstructed areas freely accessible to the operating surgeon. In particular, the areas of the outer main coronary vessels on which the operations are to be performed lie free. In other words, if the operating surgeon has correctly formed the basket from the three fingers, no further changes are needed in the course of the operation.

In cases the heart is extremely large because of pathological defects, a secure holding exceptionally needs four fingers. A fourth finger can quite simply be additionally mounted on the device since a mechanism is present anyway which fans out the strip-shaped holding fingers and in most cases locks them via a locking screw. It is then possible to additionally provide a fourth finger for exceptional cases.

The heart lies in the basket without being clamped.

The bendable design of the strip-shaped fingers allows the surgeon to form a basket of only three, or in exceptional cases four fingers, which can be adapted in situ to the anatomy of the individual heart. A basket or cage formed by the bended fingers allows a secure holding of the beating heart on the one side and exposes large areas of the beating heart for performing the surgery on the other side.

In a further embodiment of the invention, the holding fingers can be locked in a defined position.

This measure known per se has the advantage that, after forming the basket and finding the ideal position, the operating surgeon can, by locking the holding fingers, adequately fix this relative position during surgery.

In a further embodiment of the invention, the holding fingers have a slide-inhibiting surface structure on that side facing toward the heart.

This measure has the advantage that, by means of this slide-inhibiting structure, additional measures are taken to ensure that the heart does not slip out of the basket. By this means, however, it is also possible to avoid or at least substantially inhibit any rotation movements of the heart in the basket during changes in position. As the heart beats, a contraction takes place in the radial direction, and this remains possible without obstruction as before.

In a further embodiment of the invention, the surface structure has pyramid-shaped elevations.

This measure has the advantage that the tips of the pyramid-shaped elevations provide numerous but gentle points of engagement on the outside of the heart where the holding fingers are applied. This is completely atraumatic for the heart and effectively inhibits sliding.

In a further embodiment of the invention, the pyramid-shaped elevation has the base surface of a diamond.

This measure has the advantage that such a surface structure is easy to produce, and such a surface structure is also easy to clean and to sterilize.

In a further embodiment of the invention, the longer diagonal of the diamond extends in the longitudinal direction of the holding finger, and the shorter diagonal of the diamond extends in the transverse direction of the holding finger.

This measure has the advantage that the slide-inhibiting effect is greater in the transverse direction of the strip because, in the transverse direction, more pyramid-shaped elevations are present per unit of length than in the longitudinal direction. This in particular ensures that the beating heart is prevented from rotating out of the basket or from moving in the latter. The lower slide-inhibiting action in the longitudinal direction of the heart permits the natural slight axial movements of the pulsating heart. However, secure holding-up of the lifted heart is still guaranteed.

In a further embodiment of the invention, the device has at least one arm which protrudes from the securing device and at whose outer end the holding fingers are arranged.

This measure has the advantage that, between the actual heart holder and the retractor, the arm protruding from the securing device creates a space-saving connection which does not obstruct the operating field.

In a further embodiment of the invention, the arm is formed as an arm which can be moved in all directions in space.

This measure has the considerable advantage that the operating surgeon can orient the arm in a spatial direction which does not impede his range of movement during the operation or at the latest in the actual intervention on the lifted heart.

In a further embodiment of the invention, the arm can be locked in a particular spatial orientation.

This measure has the advantage that the arm can be locked and fixed after it has been suitably oriented. This also opens up the possibility of changing the orientation of the arm during the operation, that is to say while the heart is held up by the device, depending on the circumstances in situ or on the particular operating stage. The arm can be adjusted and locked in various ways. Thus, the arm can consist of several members which are movable relative to one another and which can be fixed by locking mechanisms.

It will be appreciated that the aforementioned measures and those still to be explained below can be applied not only in the specified combinations, but also in other combinations or in isolation, without departing from the scope of the present invention.

BRIEF DESCRIPTION OF THE DRAWINGS

The invention is described in greater detail and explained below on the basis of a chosen illustrative embodiment and in connection with the attached drawings, in which:

FIG. 5 shows a plan view of an end portion of a holding finger with a slide-inhibiting surface structure, FIG. 6a shows a longitudinal section of the holding finger from FIG. 5 along the long diagonal of the diamond-shaped surface structure, and FIG. 6b shows a cross section of the holding finger from FIG. 5 along the short diagonal of the diamond-shaped surface structure.

DETAILED DESCRIPTION OF A PREFERRED EMBODIMENT

Figure 1:
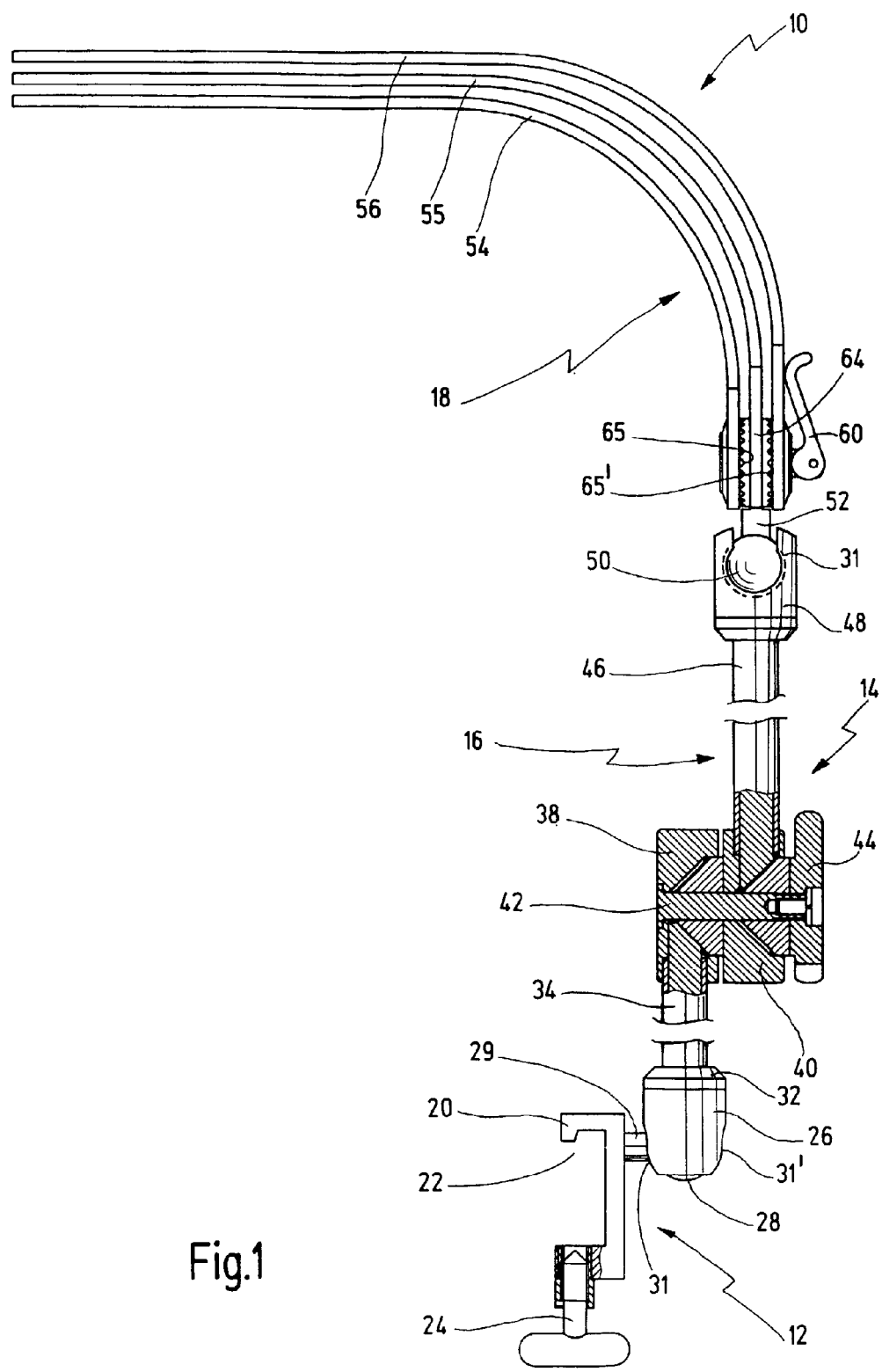
FIG. 1 shows a side view, partially in cross section, of a functional element according to the invention, having a heart holder with three holding fingers.

A functional element shown in FIG. 1 is designated overall by reference number 10.

The functional element 10 has a securing device 12 with which, as will be explained in greater detail below in connection with FIG. 4, it can be mounted on a retractor 70.

The functional element 10 also has a device 14 for holding a heart 84.

This device 14 has an arm 16 which projects from the securing device 12 and at whose outer end the actual heart holder 18 is arranged.

Figure 4:
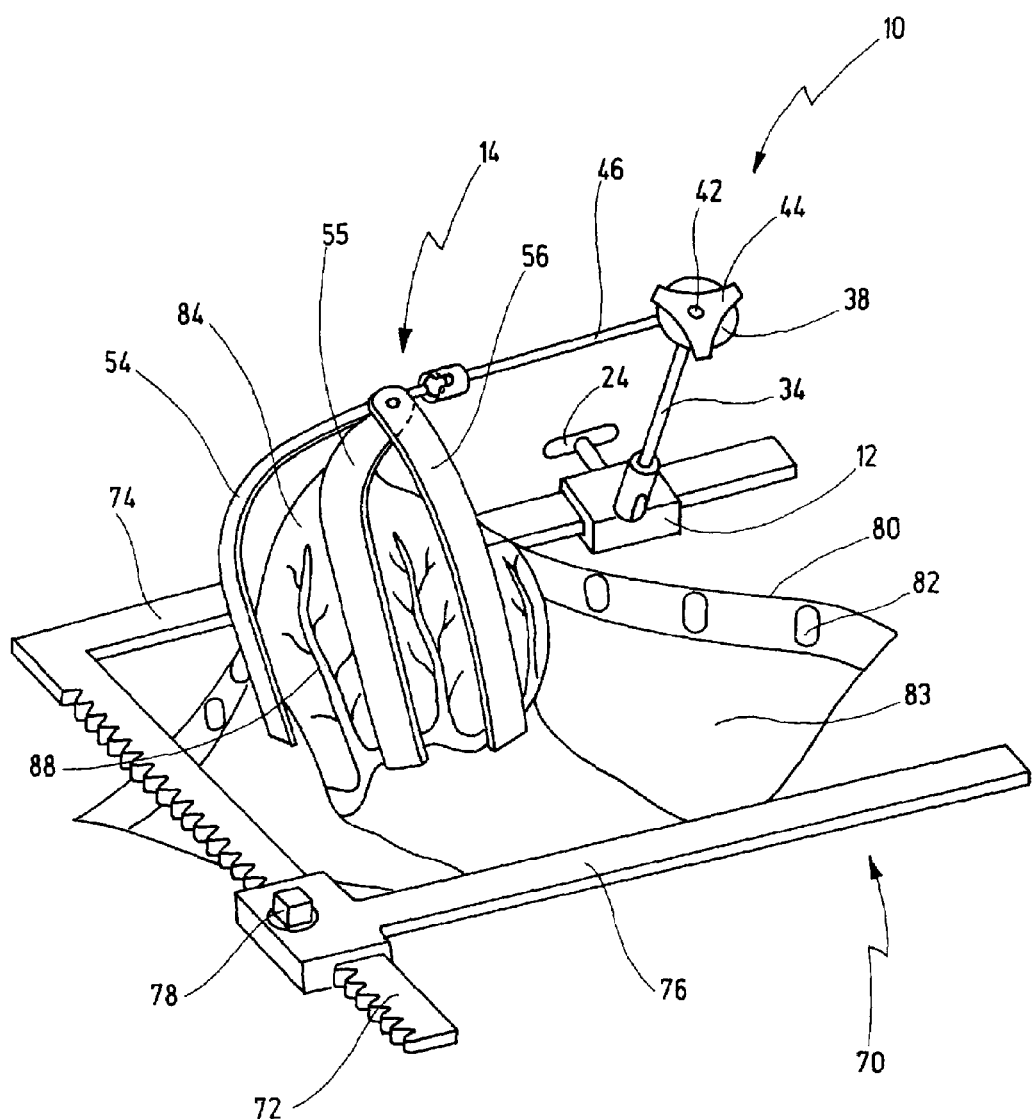
FIG. 4 shows a very diagrammatic and simplified perspective view of the use of the functional element according to the invention, mounted on a retractor, for holding a beating heart.

The securing device 12 has a block 20 in which a recess 22 is provided which corresponds to the contour of a rail 74 of the retractor 70, as can be seen from FIG. 4. The block 20 can be pushed onto the rail 74 from the outer end. A locking screw 24 is provided in order to secure the securing device 12 in position on the retractor 70.

The block 20 is connected to a first ball-and-socket joint 26.

Figure 2:
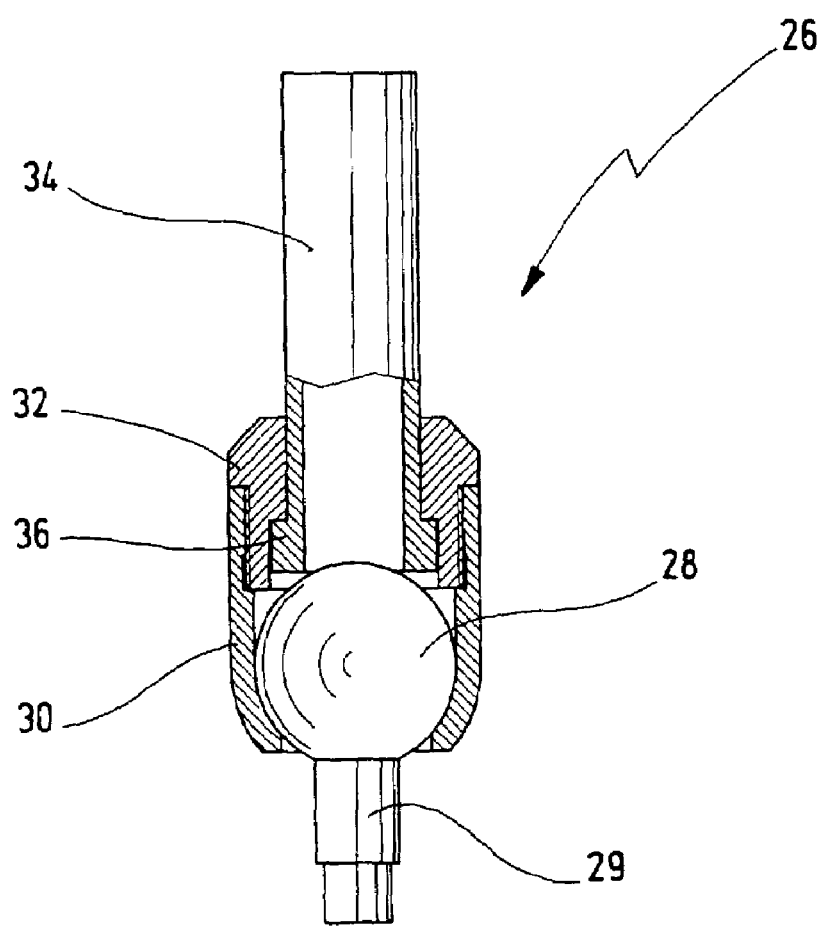
FIG. 2 shows, partially in cross section, a detailed view of a ball-and-socket joint as is used twice in the arm of the functional element.

Such a ball-and-socket joint 26 is shown on an enlarged scale in cross section in FIG. 2.

The ball 28 of the ball-and-socket joint 26 is connected to a radially projecting pin 29 via which the ball-and-socket joint 26 is connected to the outside of the block 20.

The ball 28 is received in a sleeve 30 which has two diametrically opposite U-shaped recesses 31, as can be seen in FIG. 1 for example on the upper, second ball-and-socket joint 48.

These lateral recesses 31 allow the ball 28 and pin 29 to be pivoted approximately through 180° in the sleeve 30.

A rotation ring 32 is screwed into the sleeve 30 or into an internal thread (not shown in detail).

The rotation ring accommodates a hollow bar 34, of which one end faces the ball 28 and which is provided with an annular flange 36 of greater diameter.

The rotation ring 32 rests on the step or shoulder of the annular flange 36.

FIG. 2 shows a situation in which the rotation ring 32 is screwed so far into the sleeve 30 that the bar 34 rests on the ball 28, and thus the first ball-and-socket joint 26 is locked, so that the pin 29 projecting from the ball 28 is in alignment with the bar 34.

By releasing the rotation ring 32, the ball 28 can be pivoted, for example through 90°, so that a position is then reached as shown by the ball-and-socket joint 26 in FIG. 1.

The bar 34 projecting from the sleeve 30 is connected at its opposite end to a disk 38.

This disk bears on a further disk 40 from whose side a further bar 46 projects.

The two disks 38 and 40 are connected coaxially to one another via a common continuous axle 42 and can be clamped relative to one another, i.e. locked relative to one another, via a T-screw 44 connected to the corresponding axle pin.

When the T-screw 44 is loosened, the two disks 38 and 40 can be turned relative to one another so that the two bars 34 and 46 are pivoted from the aligned orientation shown in FIG. 1 to the angled orientation as seen from FIG. 4. By screwing the T-screw 44 back in, the two disks 38 and 40 are then fixed relative to one another.

A second ball-and-socket joint 48 is arranged at the outer end of the bar 46.

The pin 52 projecting from the ball 50 of the second ball-and-socket joint 48 is connected to the actual heart holder 18.

The heart holder 18 has three holding fingers 54, 55 and 56 which consist of bent metal flat strips made of annealed surgical steel. The three holding fingers 54, 55 and 56 can each be pivoted relative to one another at one of their ends about a common axis 58. The corresponding axle pin, not detailed here, which passes through all three holding fingers 54, 55 and 56, is provided at one end with a plate 59, and at the opposite end with a clamping lever 60. The middle holding finger 55 has a body 64 which is provided at both sides with a toothing 65.

Figure 3:
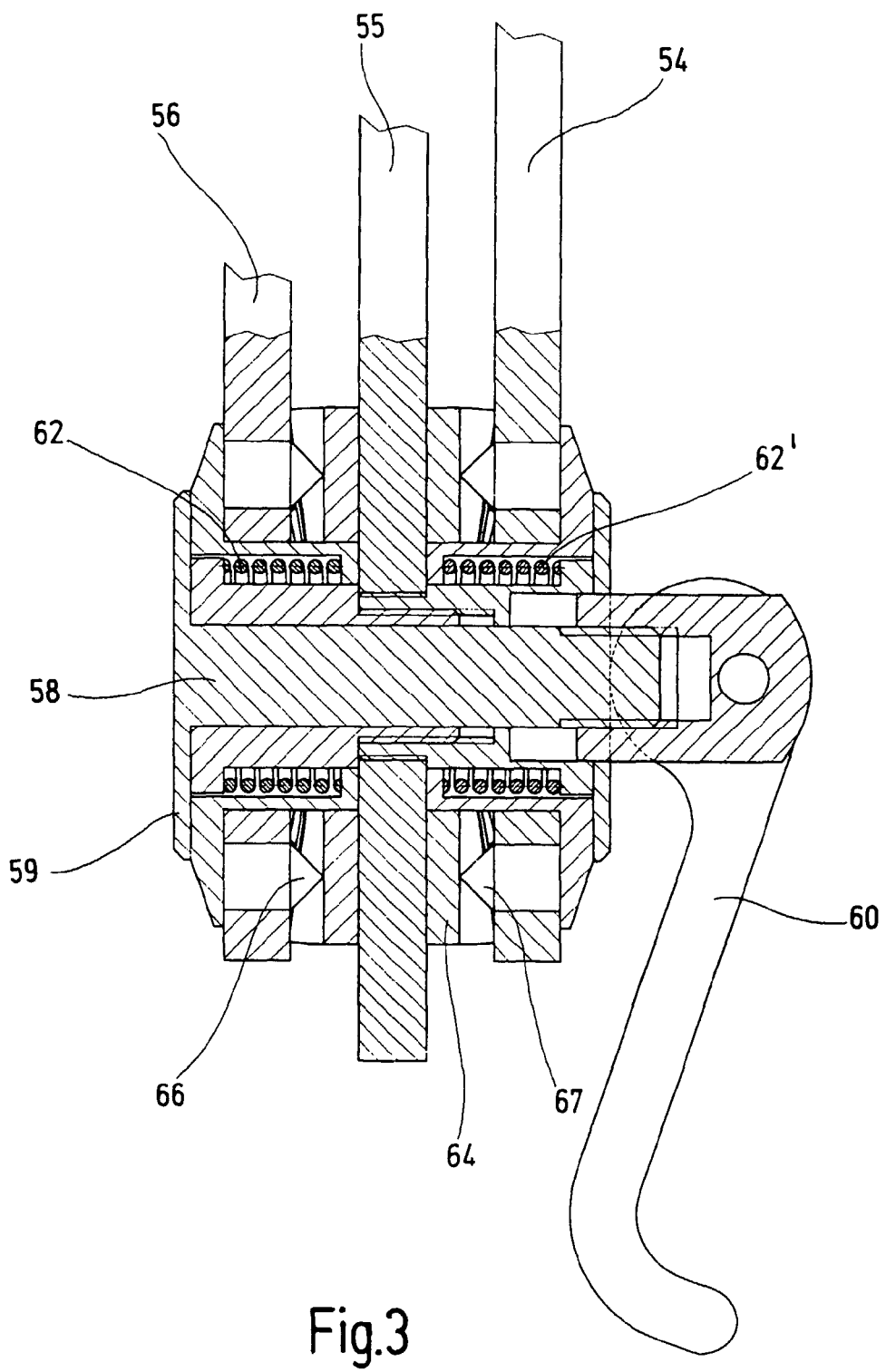
FIG. 3 shows a greatly enlarged cutaway view of an adjusting and locking mechanism for the three holding fingers.

The holding finger 56 arranged to the left of the middle holding finger 55 in the view in FIG. 3 likewise has a toothing 66 which corresponds to the toothing 65 on the body 64 and faces the latter.

Accordingly, the holding finger 54 arranged to the right of the middle holding finger 55 in the view in FIG. 3 then has a corresponding toothing 67.

Helical springs 62 and 62' are arranged between the middle holding finger 55 and each respective adjacent holding finger 54, 56, these helical springs 62 and 62' being pretensioned in such a way that each presses the respective outer holding finger 54, 56 away from the middle, positionally fixed holding finger 55.

When the clamping lever 60 is pivoted outward, the springs 62, 62' press the toothings so far apart that the three holding fingers 54, 55 and 56 can be pivoted relative to one another about the axis 58. When the clamping lever 60 is pivoted inward, the three structural elements are pressed toward one another until the toothings lock, as is shown in FIG. 1, so that the three holding fingers 54, 55 and 56 are then fixed in the corresponding position, as for example in the fanned-out position shown in FIG. 4.

The middle holding finger 55 is connected fixedly via its annular body 64 to the pin 52 of the ball-and-socket joint 48.

The way in which the functional element 10 works will be described in more detail and explained in the context of a heart surgery procedure as shown diagrammatically in FIG. 4.

The thoracic cage 80 of a patient has been opened up along the sternum, and a retractor 70 has been applied. Valves (not shown here) are mounted on the two parallel rails 74 and 76 which are displaceable relative to one another, said valves being pushed into the incision. By turning the square 78 by means of a turning lever (not shown here), the rails 74 and 76 are moved away from one another and, in doing so, the thoracic cage 80 is spread apart, as is shown in FIG. 4. In the process, the ribs 82 are also spread apart laterally, so that an opening 83 is then present in the thoracic cage 80, via which opening 83 access can be made to the heart 84 lying on one side of the thoracic cage 80.

To be able to perform a surgical procedure on a posterior wall 86 of the heart, for example on a coronary vessel 88, the heart 84 is lifted, in the area of its apex, from the thoracic cage 80 and held in this position by means of the functional element 10 according to the invention, as shown in FIG. 4. The heart 84 is still beating and is still connected to the corresponding blood vessels.

The functional element 10 according to the invention is pushed onto the rail 74 via its securing device 12 and brought to a suitable position, and the block 20 is fixed via the locking screw 24. By suitable maneuvering of the T-screw 44, the spatial orientation of the arm 16 is then brought to a favorable position, for example the angled position of the two bars 34 and 46 as shown in FIG. 4. The clamping lever 60 is then released so that the hitherto approximately congruent holding fingers 54, 55 and 56 can be spread out in a fan shape, specifically such that the apex of the lifted heart 84 is received and held between them. To do this, the operating surgeon lifts the beating heart 84 and applies the three holding fingers 54, 55 and 56 in a favorable position. By virtue of the deformability, the holding fingers 54, 55 and 56 can each be individually bent to a favorable shape so that a holding basket is finally obtained in which the beating heart 84 is held up in the lifted position. The operating surgeon then fixes the position via the toggle lever 60. In so doing, the operating surgeon positions the heart 84 so that he has good access for example to a vessel 88 of the posterior wall 86 of the heart where he wishes to perform a surgical procedure. Further functional elements are made use of in the intervention on the vessel 88, for example an OPCAB (off pump coronary artery bypass) stabilizer or a MIDCAB retractor. In the orientation of the functional element 10 shown in FIG. 4, it holds the lifted heart 84 in a fixed position but still permits a pulsating rhythmical beating of the heart 84 held in the heart holder 18.

FIGS. 5 and 6 show that a holding finger 100 is provided with a slide-inhibiting surface structure 102 on the side facing the heart 84. This slide-inhibiting surface structure 102 can of course also be provided on the above-described holding fingers 54, 55 and 56.

The slide-inhibiting surface structure 102 consists of a series of pyramid-shaped elevations 104 arranged in two-dimensional series. Each pyramid has the base surface of a diamond 106. The pyramid-shaped elevations 104 are arranged in series in such a way that, seen in the longitudinal direction of the holding finger 100, the diamonds 106 of the pyramid-shaped elevations 104 are arranged in series along their longer diagonal 108.

In the transverse direction, the diamonds 106 are arranged in series along their shorter diagonal 110.

This results in a surface structure 102 which gives slightly less slide inhibition in the longitudinal direction than in the transverse direction of the strip 100.

FIG. 6a shows a longitudinal section of the strip 100 along the longer diagonal 108, specifically over a defined unit of length. It will be seen here that four tips of the pyramid-shaped elevations are present over this unit of length.

FIG. 6b shows a cross section along the shorter diagonal 110 over the same unit of length, and it will be seen that there are eight tips of the pyramid-shaped elevations here, as is indicated by arrows in each case. This increased slide inhibition in the transverse direction ensures that, while the bition in the transverse direction ensures that, while the heart 84 does not turn in a basket formed from three strips, a certain longitudinal movement, which takes place as the heart beats, is still inhibited to a lesser extent.

On completion of the surgical procedure, the holding fingers 54, 55 and 56 or 100 are released again, the heart 84 is put back into the thoracic cage 80, and the thoracic cage is then closed.

What is claimed is:

1. A functional element to be mounted on a retractor for performing cardiothoracic surgery, comprising
   a securing device for mounting it releasibly on a retractor, and
   a device for holding up a beating heart lifted from an operating site of a cardiothoracic surgery,
   said device having a number selected from three or four spreadable strip-shaped holding fingers, each of said fingers being bendable by a surgeon for forming a holding basket in situ that is adapted to a shape of a heart which is to be held by said basket, wherein said spreadable fingers are mounted pivotally relative to one another, and can be locked in a defined position of pivoting via a locking device.

2. Functional element of claim 1, wherein said device has at least one arm protruding from said securing device, said holding fingers are arranged at an outer end of said arm.

3. Functional element of claim 2, wherein said arm is designed as an arm movable in all directions in space.

4. Functional element of claim 3, wherein said arm can be locked in a particular spatial orientation.

5. Functional element of claim 1, wherein said fingers are provided with a slide-inhibiting surface structure on a side facing toward said beating heart to be hold.

6. Functional element of claim 5, wherein said slide-inhibiting surface structure has pyramid-shaped elevations elevating from said side facing toward said beating heart.

7. Functional element of claim 6, wherein said pyramid-shaped elevation having a base surface of a diamond.

8. Functional element of claim 7, wherein said diamond having a longer diagonal extending in a longitudinal direction of said holding fingers, and a shorter diagonal extending in a transverse direction of said holding fingers.

* * * * *